(12) United States Patent
Song et al.

(10) Patent No.: US 9,492,507 B2
(45) Date of Patent: Nov. 15, 2016

(54) INSULIN CONJUGATE USING AN IMMUNOGLOBULIN FRAGMENT

(75) Inventors: Dae Hae Song, Hwaseong-si (KR); Jae Hee Shin, Suwon-si (KR); Young Jin Park, Suwon-si (KR); Dae Seong Im, Yongin-si (KR); Sung Min Bae, Seongnam-si (KR); Se Chang Kwon, Seoul (KR)

(73) Assignee: HANMI SCIENCE CO., LTD., Hwaseong-si (KR)

( * ) Notice: Subject to any disclaimer, the term of this patent is extended or adjusted under 35 U.S.C. 154(b) by 0 days.

(21) Appl. No.: 13/638,786

(22) PCT Filed: Apr. 4, 2011

(86) PCT No.: PCT/KR2011/002331
§ 371 (c)(1),
(2), (4) Date: Oct. 1, 2012

(87) PCT Pub. No.: WO2011/122921
PCT Pub. Date: Oct. 6, 2011

(65) Prior Publication Data
US 2013/0028918 A1    Jan. 31, 2013

(30) Foreign Application Priority Data

Apr. 2, 2010  (KR) .................. 10-2010-0030575

(51) Int. Cl.
C07K 14/62 (2006.01)
A61K 38/28 (2006.01)
A61K 47/48 (2006.01)

(52) U.S. Cl.
CPC .......... *A61K 38/28* (2013.01); *A61K 47/48369* (2013.01); *A61K 47/48692* (2013.01); *C07K 14/62* (2013.01); *C07K 2319/30* (2013.01)

(58) Field of Classification Search
CPC .......................... C07K 14/62; C07K 2319/30
USPC ........................................................ 514/303
See application file for complete search history.

(56) References Cited

U.S. PATENT DOCUMENTS

| | | | |
|---|---|---|---|
| 6,756,480 B2 | 6/2004 | Kostenuik et al. | |
| 6,924,264 B1 | 8/2005 | Prickett et al. | |
| 2003/0012789 A1 | 1/2003 | Blumberg et al. | |
| 2004/0062748 A1 | 4/2004 | Martinez et al. | |
| 2006/0183197 A1* | 8/2006 | Andersen et al. | 435/69.4 |
| 2007/0041972 A1* | 2/2007 | Rother et al. | 424/145.1 |
| 2007/0042954 A1 | 2/2007 | Chen et al. | |
| 2007/0083006 A1 | 4/2007 | Hinds et al. | |
| 2008/0124347 A1* | 5/2008 | Kim et al. | 424/179.1 |
| 2008/0280818 A1 | 11/2008 | DeFrees | |
| 2009/0104210 A1 | 4/2009 | Tota et al. | |
| 2009/0238838 A1 | 9/2009 | Kim et al. | |
| 2009/0285780 A1 | 11/2009 | Lee | |
| 2010/0055733 A1 | 3/2010 | Lutolf et al. | |

FOREIGN PATENT DOCUMENTS

| | | |
|---|---|---|
| CN | 1133598 A | 10/1996 |
| CN | 1582171 A | 2/2005 |
| CN | 1723219 A | 1/2006 |
| CN | 101646451 A | 2/2010 |
| JP | 2007-531513 A | 11/2007 |
| JP | 2008-534676 A | 8/2008 |
| KR | 10-2005-0047032 A | 5/2005 |
| TW | 201004649 A | 2/2010 |
| WO | 95/07931 A1 | 3/1995 |
| WO | 02/46227 A2 | 6/2002 |
| WO | 02/094200 A2 | 11/2002 |
| WO | 2005/047334 A1 | 5/2005 |
| WO | 2005/047336 A1 | 5/2005 |
| WO | 2005/047337 A1 | 5/2005 |
| WO | 2006/076471 A2 | 7/2006 |
| WO | 2006/107124 A1 | 10/2006 |
| WO | 2008/082274 A1 | 7/2008 |
| WO | 2008/084051 A1 | 7/2008 |
| WO | 2009/152128 A1 | 12/2009 |
| WO | 2010/011096 A2 | 1/2010 |
| WO | 2011/122921 A2 | 10/2011 |
| WO | 2011/122921 A3 | 10/2011 |

OTHER PUBLICATIONS

Harris et al., Nature 2: 214-221, 2003.*
International Searching Authority, International Search Report for PCT/KR2011/002331 dated Dec. 21, 2011.
International Searching Authority, Written Opinion for PCT/KR2011/002331 dated Dec. 21, 2011.
Hinds et al., "Effects of PEG Conjugation on Insulin Properties," Advanced Drug Delivery Reviews, 2002, vol. 54, pp. 505-530.
Korean Patent Office, Korean Office Action issued in corresponding KR Application No. 10-2011-0030868, dated Feb. 22, 2013.
Japanese Patent Office, Office Action dated Jun. 3, 2014 in corresponding Japanese Patent Application No. 2013-502499.
Taiwanese Patent Office, Office Action dated Apr. 17, 2014, in corresponding Taiwanese Patent Application No. 100111784.
State Intellectual Property Office of the People's Republic of China, Office Action dated Apr. 4, 2014 in corresponding Chinese Patent Application No. 201180022035.X.
European Patent Office, Communication dated Jan. 24, 2014, issued in corresponding European Application No. 11763093.9.
Russian Patent Office, Communication dated Oct. 16, 2013, issued in corresponding Russian Application No. 2012146663/15(074998).
Intellectual Property Corporation of Malaysia, Communication dated Sep. 30, 2013, issued in corresponding Malaysian Application No. PI 2012004365.
State Intellectual Property Office of the People's Republic of China, Communication dated Jul. 22, 2013, issued in corresponding Chinese Application No. 201180022035.X.
Taiwanese Patent Office, Communication dated Jul. 18, 2013, issued in corresponding Taiwanese Application No. 100111784.
Mexico Patent Office, Communication dated Apr. 14, 2015, issued in corresponding Mexican Application No. MX/a/2012/011384.

* cited by examiner

*Primary Examiner* — Gyan Chandra
(74) *Attorney, Agent, or Firm* — Sughrue Mion, PLLC (57) ABSTRACT

The present invention relates to an insulin conjugate having improved in vivo duration and stability, which is prepared by covalently linking insulin with an immunoglobulin Fc region via a non-peptidyl polymer, a long-acting formulation comprising the same, and a preparation method thereof. The insulin conjugate of the present invention maintains in vivo activity of the peptide at a relatively high level and remarkably increases the serum half-life thereof, thereby greatly improving drug compliance upon insulin treatment.

17 Claims, 5 Drawing Sheets

INSULIN CONJUGATE USING AN IMMUNOGLOBULIN FRAGMENT

CROSS REFERENCE TO RELATED APPLICATIONS

This application is a National Stage of International Application No. PCT/KR2011/002331, filed on Apr. 4, 2011, which claims priority from Korean Patent Application No. 10-2010-0030575 filed on Apr. 2, 2010, the contents of all of which are incorporated herein by reference in their entirety.

TECHNICAL FIELD

The present invention relates to an insulin conjugate having improved in vivo duration and stability, which is prepared by covalently linking insulin with an immunoglobulin Fc region via a non-peptidyl polymer, a long-acting formulation comprising the same, and a preparation method thereof. The invention provides method for treating in a subject having a insulin-deficiency disorder, such as diabetes. The insulin conjugate of the present invention maintains in vivo activity of the peptide at a relatively high level and remarkably increases the serum half-life thereof, thereby greatly improving drug compliance upon insulin treatment.

BACKGROUND ART

Insulin, a peptide secreted by the pancreatic beta cells, plays a central role in the control of blood glucose levels in the body. When insulin is not properly secreted or the secreted insulin does not work in the body, the blood glucose level is not regulated, and thus diabetes occurs. This diabetes is called type II diabetes. Type I diabetes is caused when the pancreas does not make enough insulin to increase the blood glucose level.

Type II diabetes is usually treated with oral hypoglycemic agents chemically synthesized, and in some cases, patients are treated with insulin. Meanwhile, type I diabetes requires insulin treatment.

The insulin treatment method currently used is injection of insulin before/after meals. However, such insulin injection should be continuously administered three times per day, which causes pain or discomfort to the patients. There have been various attempts to overcome the problem. One of them is a method of delivering a peptide drug via oral or nasal inhalation by improving its membrane permeability. Undesirably, the method showed very low delivery efficiency, compared to the injectable formulations, and thus there are still many difficulties in maintaining in vivo activity of the peptide drug at the required level.

Meanwhile, there was a method of delaying drug absorption after a subcutaneous injection of a large amount of the drug, so as to maintain the blood level by only one daily injection. Some of the developed drugs (Lantus, Sanofi-aventis) were approved, and are now used for the patients. In addition, studies have been conducted to prolong the action, leading to development of Levemir (Novo Nordisk) prepared by modification of insulin with fatty acid, in which the protracted action occurs through self-association of insulin molecules at the site of injection and through reversible binding to albumin in the blood. However, these methods generate pains at the site of injection, and the daily injections also cause considerable discomfort to the patient.

Many efforts have been made to improve the serum stability of peptide drugs and maintain the drugs in the blood at high levels for a prolonged period of time, thereby maximizing the pharmaceutical efficacy of the drugs. These long-acting formulations of peptide drugs need to increase the stability of the peptide drugs and maintain the titers at sufficiently high levels without causing immune responses in patients. For the preparation of the long-acting formulations of peptide drugs, a polymer having high solubility, such as polyethylene glycol (PEG), was conventionally used to chemically modify the surface of a peptide drug.

PEG non-specifically binds to a specific site or various sites of a target peptide to give an effect of increasing the molecular weight of a peptide, and thus inhibiting the loss by the kidney, and preventing hydrolysis, without causing any side-effects. For example, WO 2006/076471 describes that a B-type natriuretic peptide (BNP), which binds to NPR-A to activate the production of cGMP and leads to reduction in the arterial blood pressure, and as a result, is used as a congestive heart failure therapeutic agent, is linked to PEG, thereby sustaining its physiological activity. U.S. Pat. No. 6,924,264 describes that PEG binds to the lysine residue of an exendin-4 to increase its in-vivo residence time. This method increases the molecular weight of PEG, and thus increases the in-vivo residence time of the peptide drug. However, as the molecular weight is increased, the titer of the peptide drug is remarkably reduced, and the reactivity with the peptide is also reduced. Accordingly, it undesirably lowers the yield.

WO 02/46227 describes a fusion protein prepared by coupling GLP-1, an exendin-4, or an analog thereof with human serum albumin or an immunoglobulin fragment (Fc) using a genetic recombination technology. U.S. Pat. No. 6,756,480 describes an Fc fusion protein prepared by coupling a parathyroid hormone (PTH) and an analog thereof with Fc region. These methods can address the problems such as low pegylation yield and non-specificity, but they still have a problem in that the effect of increasing the blood half-life is not as noticeable as expected, and in some cases, the titers are also low. In order to maximize the effect of increasing the blood half-life, various kinds of peptide linkers have been used, but there is a possibility of causing an immune response. Further, if a peptide having disulfide bonds, such as BNP, is used, there is a high probability of misfolding, and if a peptide having non-naturally occurring amino acid residues is used, it can be produced by genetic recombination only with great difficulty.

DISCLOSURE

Technical Problem

In this regard, leading to the present invention, intensive and thorough research into the development of a method capable of simultaneously maximizing the serum half-life and in vivo activity of insulin has been undergone, resulted in the finding that an immunoglobulin Fc region, a non-peptidyl polymer, and insulin are site-selectively linked to each other by a covalent bond, thereby remarkably increasing the serum half-life, compared to the known inframe fusion method.

Technical Solution

It is an object of the present invention to provide an excellent insulin conjugate that maintains in vivo activity of insulin and remarkably prolongs the serum half-life thereof, a long-acting formulation comprising the same, and a preparation method thereof.

Advantageous Effects

The insulin conjugate of the present invention maintains in vivo activity of peptide at a relatively high level and remarkably increases the serum half-life thereof, thereby greatly improving drug compliance of patients in need of insulin treatment.

BEST MODE

In one aspect to achieve the above objects, the present invention provides an insulin conjugate that is prepared by linking insulin with an immunoglobulin Fc region via a non-peptidyl polymer, in which the non-peptidyl polymer is linked to the amino terminus of the beta chain of insulin.

In the present invention, insulin is a peptide that is secreted by the pancreas in response to elevated glucose levels in the blood to take up glucose in the liver, muscle, or adipose tissue and turn it into glycogen, and to stop the use of fat as an energy source, and thus functions to control the blood glucose level. This peptide includes agonists, precursors, derivatives, fragments, and variants thereof, and preferably native, short-acting, or long-acting insulin.

Native insulin is a hormone that is secreted by the pancreas to promote glucose absorption and inhibit fat breakdown, and thus functions to control the blood glucose level. Insulin is formed from a precursor having no function of regulating the blood glucose level, known as proinsulin, through processing. The amino acid sequences of insulin are as follows:

Alpha chain:
(SEQ ID NO. 1)
Gly-Ile-Val-Glu-Gln-Cys-Cys-Thr-Ser-Ile-Cys-Ser-

Leu-Tyr-Gln-Leu-Glu-Asn-Tyr-Cys-Asn

Beta chain:
(SEQ ID NO. 2)
Phe-Val-Asn-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Pro-Lys-Thr

The insulin agonist means a compound that binds to the insulin receptor to show the biological activity equal to that of insulin, which is irrelevant to the structure of insulin.

The insulin derivative means a peptide having at least 80% amino acid sequence homology with the native insulin, which may have some groups on the amino acid residue chemically substituted (e.g., alpha-methylation, alpha-hydroxylation), deleted (e.g., deamination), or modified (e.g., N-methylation), and has a function of regulating the blood glucose level in the body.

The insulin fragment means a fragment having one or more amino acids added or deleted at the N-terminus or the C-terminus of the native insulin, in which non-naturally occurring amino acids (for example, D-type amino acid) can be added, and has a function of regulating the blood glucose level in the body.

The insulin variant means a peptide having one or more amino acid sequence different from that of the native insulin, and having a function of regulating the blood glucose level in the body.

Each of the preparation methods for the agonists, derivatives, fragments, and variants of insulin can be used individually or in combination. For example, the present invention includes a peptide that has one or more amino acids different from those of native peptide and deamination of the N-terminal amino acid residue, and has a function of regulating the blood glucose level in the body.

In a specific embodiment, the insulin used in the present invention may be produced by a recombination technology, and may be also synthesized using a solid phase synthesis method.

Further, the insulin used in the present invention is characterized in that a non-peptidyl polymer is linked to the amino terminus of the beta chain of insulin. This non-peptidyl polymer is used as a linker in the present invention. The modification in the alpha chain of insulin leads to a reduction in the activity and safety. In the present invention, therefore, the non-peptidyl polymer as a linker is linked to the amino terminus of beta chain of insulin, so as to maintain the insulin activity and improve safety.

The term "activity", as used herein, means the ability of insulin to bind to the insulin receptor, and means that insulin exhibits its action through binding to insulin receptor.

Such binding of non-peptidyl polymer to the amino terminus of beta chain of insulin can be achieved by pH control, and preferably, in the range from 4.5 to 7.5.

The term "N-terminus", as used herein, can be used interchangeably with "N-terminal region".

In one specific Example, the present inventors prepared an insulin-PEG-immunoglobulin Fc conjugate by linking PEG to the N-terminus of an immunoglobulin Fc region, and selectively coupling the N-terminus of the beta chain of insulin thereto. The serum half-life of the insulin-PEG-immunoglobulin Fc conjugate prepared in the present invention was remarkably increased to approximately 18 hrs, and it showed a hypoglycemic effect in disease animal models. Therefore, a new long-acting insulin formulation that maintains in vivo activity of insulin can be prepared.

The immunoglobulin Fc region is safe for use as a drug carrier because it is a biodegradable polypeptide that is in vivo metabolized. Also, the immunoglobulin Fc region has a relatively low molecular weight, as compared to the whole immunoglobulin molecules, and thus, it is advantageous in the preparation, purification and yield of the conjugate. The immunoglobulin Fc region does not contain a Fab fragment, which is highly non-homogenous due to different amino acid sequences according to the antibody subclasses, and thus it can be expected that the immunoglobulin Fc region may greatly increase the homogeneity of substances and be less antigenic.

The term "immunoglobulin Fc region", as used herein, refers to a protein that contains the heavy-chain constant region 2 (CH2) and the heavy-chain constant region 3 (CH3) of an immunoglobulin, excluding the variable regions of the heavy and light chains, the heavy-chain constant region 1 (CH1) and the light-chain constant region 1 (CL1) of the immunoglobulin. It may further include a hinge region at the heavy-chain constant region. Also, the immunoglobulin Fc region of the present invention may contain a part or all of the Fc region including the heavy-chain constant region 1 (CH1) and/or the light-chain constant region 1 (CL1), except for the variable regions of the heavy and light chains, as long as it has a physiological function substantially similar to or better than the native protein. Also, it may be a fragment having a deletion in a relatively long portion of the amino acid sequence of CH2 and/or CH3. That is, the immunoglobulin Fc region of the present invention may comprise 1) a CH1 domain, a CH2 domain, a CH3 domain and a CH4 domain, 2) a CH1 domain and a CH2 domain, 3) a CH1 domain and a CH3 domain, 4) a CH2 domain and a CH3 domain, 5) a combination of one or more domains and an immunoglobulin hinge region (or a portion of the hinge region), and 6) a dimer of each domain of the heavy-chain constant regions and the light-chain constant region.

Further, the immunoglobulin Fc region of the present invention includes a sequence derivative (mutant) thereof as well as a native amino acid sequence. An amino acid sequence derivative has a sequence that is different from the native amino acid sequence due to a deletion, an insertion, a non-conservative or conservative substitution or combinations thereof of one or more amino acid residues. For example, in an IgG Fc, amino acid residues known to be important in binding, at positions 214 to 238, 297 to 299, 318 to 322, or 327 to 331, may be used as a suitable target for modification. In addition, other various derivatives are possible, including derivatives having a deletion of a region capable of forming a disulfide bond, a deletion of several amino acid residues at the N-terminus of a native Fc form, or an addition of methionine residue to the N-terminus of a native Fc form. Furthermore, to remove effector functions, a deletion may occur in a complement-binding site, such as a C1q-binding site and an ADCC site. Techniques of preparing such sequence derivatives of the immunoglobulin Fc region are disclosed in WO 97/34631 and WO 96/32478.

Amino acid exchanges in proteins and peptides, which do not generally alter the activity of molecules, are known in the art (H. Neurath, R. L. Hill, The Proteins, Academic Press, New York, 197 9). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly, in both directions.

The Fc region, if desired, may be modified by phosphorylation, sulfation, acrylation, glycosylation, methylation, farnesylation, acetylation, amidation, and the like.

The aforementioned Fc derivatives are derivatives that have a biological activity identical to that of the Fc region of the present invention or improved structural stability, for example, against heat, pH, or the like.

In addition, these Fc regions may be obtained from native forms isolated from humans and other animals including cows, goats, swine, mice, rabbits, hamsters, rats and guinea pigs, or may be recombinants or derivatives thereof, obtained from transformed animal cells or microorganisms. Herein, they may be obtained from a native immunoglobulin by isolating whole immunoglobulins from human or animal organisms and treating them with a proteolytic enzyme. Papain digests the native immunoglobulin into Fab and Fc regions, and pepsin treatment results in the production of pF'c and F(ab)2 fragments. These fragments may be subjected, for example, to size-exclusion chromatography to isolate Fc or pF'c.

Preferably, a human-derived Fc region is a recombinant immunoglobulin Fc region that is obtained from a microorganism.

In addition, the immunoglobulin Fc region of the present invention may be in the form of having native sugar chains, increased sugar chains compared to a native form or decreased sugar chains compared to the native form, or may be in a deglycosylated form. The increase, decrease or removal of the immunoglobulin Fc sugar chains may be achieved by methods common in the art, such as a chemical method, an enzymatic method and a genetic engineering method using a microorganism. The removal of sugar chains from an Fc region results in a sharp decrease in binding affinity to the complement (c1q) and a decrease or loss in antibody-dependent cell-mediated cytotoxicity or complement-dependent cytotoxicity, thereby not inducing unnecessary immune responses in-vivo. In this regard, an immunoglobulin Fc region in a deglycosylated or aglycosylated form may be more suitable to the object of the present invention as a drug carrier.

The term "deglycosylation", as used herein, means to enzymatically remove sugar moieties from an Fc region, and the term "aglycosylation" means that an Fc region is produced in an unglycosylated form by a prokaryote, preferably E. coli.

In addition, the immunoglobulin Fc region may be an Fc region that is derived from IgG, IgA, IgD, IgE and IgM, or that is made by combinations thereof or hybrids thereof. Preferably, it is derived from IgG or IgM, which is among the most abundant proteins in the human blood, and most preferably from IgG, which is known to enhance the half-life of ligand-binding proteins.

The term "combination", as used herein, means that polypeptides encoding single-chain immunoglobulin Fc regions of the same origin are linked to a single-chain polypeptide of a different origin to form a dimer or multimer. That is, a dimer or multimer may be formed from two or more fragments selected from the group consisting of IgG Fc, IgA Fc, IgM Fc, IgD Fc, and IgE Fc fragments.

The term "hybrid", as used herein, means that sequences encoding two or more immunoglobulin Fc regions of different origin are present in a single-chain immunoglobulin Fc region. In the present invention, various types of hybrids are possible. That is, domain hybrids may be composed of one to four domains selected from the group consisting of CH1, CH2, CH3 and CH4 of IgG Fc, IgM Fc, IgA Fc, IgE Fc and IgD Fc, and may include the hinge region.

On the other hand, IgG is divided into IgG1, IgG2, IgG3 and IgG4 subclasses, and the present invention includes combinations or hybrids thereof. Preferred are IgG2 and IgG4 subclasses, and most preferred is the Fc region of IgG4 rarely having effector functions such as CDC (complement dependent cytotoxicity).

As the drug carrier of the present invention, the most preferable immunoglobulin Fc region is a human IgG4-derived non-glycosylated Fc region. The human-derived Fc region is more preferable than a non-human derived Fc region, which may act as an antigen in the human body and cause undesirable immune responses such as the production of a new antibody against the antigen.

The term "non-peptidyl polymer", as used herein, refers to a biocompatible polymer including two or more repeating units linked to each other by any covalent bond excluding a peptide bond.

The non-peptidyl polymer which can be used in the present invention may be selected form the group consisting of polyethylene glycol, polypropylene glycol, copolymers of ethylene glycol and propylene glycol, polyoxyethylated polyols, polyvinyl alcohol, polysaccharides, dextran, polyvinyl ethyl ether, biodegradable polymers such as PLA (poly(lactic acid)) and PLGA (polylactic-glycolic acid), lipid polymers, chitins, hyaluronic acid, and combinations thereof, and preferably, polyethylene glycol. The derivatives thereof well known in the art and being easily prepared within the skill of the art are also included in the scope of the present invention.

The peptide linker which is used in the fusion protein obtained by a conventional inframe fusion method has drawbacks in that it is easily in-vivo cleaved by a proteolytic enzyme, and thus a sufficient effect of increasing the serum half-life of the active drug by a carrier cannot be obtained as expected. However, in the present invention, the polymer having resistance to the proteolytic enzyme can be used to maintain the serum half-life of the peptide being similar to that of the carrier. Therefore, any non-peptidyl polymer can be used without any limitation, as long as it is a polymer having the aforementioned function, that is, a polymer having resistance to the in-vivo proteolytic enzyme. The non-peptidyl polymer has a molecular weight in the range of 1 to 100 kDa, and preferably of 1 to 20 kDa. The non-peptidyl polymer of the present invention, linked to the immunoglobulin Fc region, may be one polymer or a combination of different types of polymers.

The non-peptidyl polymer used in the present invention has a reactive group capable of binding to the immunoglobulin Fc region and protein drug.

The non-peptidyl polymer has a reactive group at both ends, which is preferably selected from the group consisting of a reactive aldehyde group, a propionaldehyde group, a butyraldehyde group, a maleimide group and a succinimide derivative. The succinimide derivative may be succinimidyl propionate, hydroxy succinimidyl, succinimidyl carboxymethyl, or succinimidyl carbonate. In particular, when the non-peptidyl polymer has a reactive aldehyde group at both ends thereof, it is effective in linking at both ends with a physiologically active polypeptide and an immunoglobulin with minimal non-specific reactions. A final product generated by reductive alkylation by an aldehyde bond is much more stable than that linked by an amide bond. The aldehyde reactive group selectively binds to an N-terminus at a low pH, and binds to a lysine residue to form a covalent bond at a high pH, such as pH 9.0.

The reactive groups at both ends of the non-peptidyl polymer may be the same or different. For example, the non-peptide polymer may possess a maleimide group at one end, and an aldehyde group, a propionaldehyde group or a butyraldehyde group at the other end. When a polyethylene glycol having a reactive hydroxy group at both ends thereof is used as the non-peptidyl polymer, the hydroxy group may be activated to various reactive groups by known chemical reactions, or a polyethylene glycol having a commercially available modified reactive group may be used so as to prepare the protein conjugate of the present invention.

In another aspect of the present invention, the present invention provides a long-acting insulin formulation comprising the insulin conjugate of the present invention.

The term "administration", as used herein, means introduction of a predetermined amount of a substance into a patient by a certain suitable method. The conjugate may be administered via any of the common routes, as long as it is able to reach a desired tissue. A variety of modes of administration are contemplated, including intraperitoneally, intravenously, intramuscularly, subcutaneously, intradermally, orally, topically, intranasally, intrapulmonarily and intrarectally, but the present invention is not limited to these exemplified modes of administration. However, since peptides are digested upon oral administration, active ingredients of a composition for oral administration should be coated or formulated for protection against degradation in the stomach. Preferably, the conjugate may be administered in an injectable form. In addition, the long-acting formulation may be administered using a certain apparatus capable of transporting the active ingredients into a target cell.

The long-acting formulation comprising the conjugate of the present invention may include pharmaceutically acceptable carriers. For oral administration, the pharmaceutically acceptable carrier may include a binder, a lubricant, a disintegrator, an excipient, a solubilizer, a dispersing agent, a stabilizer, a suspending agent, a coloring agent, and a perfume. For injectable preparations, the pharmaceutically acceptable carrier may include a buffering agent, a preserving agent, an analgesic, a solubilizer, an isotonic agent, and a stabilizer. For preparations for topical administration, the pharmaceutically acceptable carrier may include a base, an excipient, a lubricant, and a preserving agent. The long-acting formulation of the present invention may be formulated into a variety of dosage forms in combination with the aforementioned pharmaceutically acceptable carriers. For example, for oral administration, the long-acting formulation may be formulated into tablets, troches, capsules, elixirs, suspensions, syrups or wafers. For injectable preparations, the long-acting formulation may be formulated into single-dose ampule or multidose container. The long-acting formulation may be also formulated into solutions, suspensions, tablets, pills, capsules and sustained release preparations.

Examples of the carrier, the excipient, and the diluent suitable for the formulations include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the formulations may further include fillers, anti-coagulating agents, lubricants, humectants, perfumes, and antiseptics.

The long-acting formulation of the present invention can be determined by several related factors including the types of diseases to be treated, administration routes, the patient's age, gender, weight and severity of the illness, as well as by the types of the drug as an active component. Since the pharmaceutical composition of the present invention has excellent in vivo duration and titer, it can remarkably reduce the administration frequency and dose of pharmaceutical drugs of the present invention.

The long-acting formulation of the present invention maintains in vivo duration and stability of insulin at a very high level, and thus effectively used for the treatment of insulin-dependent diabetes.

In still another aspect, the present invention provides a method for preparing an insulin conjugate, comprising the steps of:
(1) covalently linking a non-peptidyl polymer having a reactive group of aldehyde, maleimide, or succinimide derivatives at each end thereof, with an amine group or thiol group of the immunoglobulin Fc region;

(2) isolating a conjugate from the reaction mixture of (1), in which the conjugate comprises the immunoglobulin Fc region covalently linked with the non-peptidyl polymer; and
(3) covalently linking insulin to the other end of the non-peptidyl polymer of the isolated conjugate to produce a peptide conjugate comprising the immunoglobulin Fc region and insulin, which are linked to each end of the non-peptidyl polymer.

Preferably, the non-peptidyl polymer of step (1) has a reactive aldehyde derivative at the end thereof, and more preferably, three reactive aldehyde groups.

In still another aspect, the present invention provides a method for preparing an insulin conjugate, comprising the steps of:
(1) covalently linking a non-peptidyl polymer having an aldehyde reactive group at each end thereof to the N-terminus of the immunoglobulin Fc at pH 6.0;
(2) isolating a conjugate from the reaction mixture of (1), in which the conjugate comprises the immunoglobulin Fc region covalently linked with the non-peptidyl polymer at its N-terminus; and
(3) covalently linking insulin to the other end of the non-peptidyl polymer of the isolated conjugate to produce a peptide conjugate comprising the immunoglobulin Fc region and insulin, which are linked to each end of the non-peptidyl polymer.

In still another aspect, the present invention provides a method for preparing an insulin conjugate, comprising the steps of:
(1) covalently linking a non-peptidyl polymer having a reactive group of aldehyde, maleimide, or succinimide derivatives at each end thereof, with an amine group or thiol group of insulin;
(2) isolating a conjugate from the reaction mixture of (1), in which the conjugate comprises insulin covalently linked with the non-peptidyl polymer; and
(3) covalently linking an immunoglobulin Fc region to the other end of the non-peptidyl polymer of the isolated conjugate to produce a peptide conjugate comprising the immunoglobulin Fc region and insulin, which are linked to each end of the non-peptidyl polymer.

In still another aspect, the present invention provides a method for preparing an insulin conjugate, comprising the steps of:
(1) covalently linking a non-peptidyl polymer having an aldehyde reactive group at each end thereof with an amine group of insulin;
(2) isolating a conjugate from the reaction mixture of (1), in which the conjugate comprises insulin covalently linked with the non-peptidyl polymer; and
(3) covalently linking an immunoglobulin Fc region to the other end of the non-peptidyl polymer of the isolated conjugate to produce a peptide conjugate comprising the immunoglobulin Fc region and insulin, which are linked to each end of the non-peptidyl polymer.

In still another aspect, the present invention provides a method for treating a subject having a insulin-deficiency disorder, the method comprising of administering to the subject an effective amount of the long-acting formulation. Preferably, the insulin-deficiency disorder is diabetes.

As used herein, a subject can be a mammal, for example, human, a non-human primate, a horse, a sheep, a cat, a dog, a cow or a pig.

MODE FOR INVENTION

Hereinafter, a better understanding of the present invention may be obtained through the following Examples which are set forth to illustrate, but are not to be construed as the limit of the present invention.

Example 1

Purification of Pegylated Immunoglobulin Fc Region

For pegylation of the immunoglobulin Fc at its N-terminus, 5K PropionALD (3) PEG (PEG having three propylaldehyde groups, NOF, Japan) was used to perform pegylation by reacting the immunoglobulin Fc and PEG at 4° C. for 4.5 hrs and at a molar ratio of 1:2, with an immunoglobulin Fc concentration of 10 mg/ml. At this time, the reaction was performed in a 100 mM potassium phosphate buffer solution at pH 6.0, and 20 mM SCB (NaCNBH$_3$) as a reducing agent was added thereto. A mono-PEGylated immunoglobulin Fc was purified from the reaction solution using a Source 15Q (GE Healthcare) column.

Example 2

Preparation of Insulin-PEG-Immunoglobulin Fc Conjugate

Figure 3:
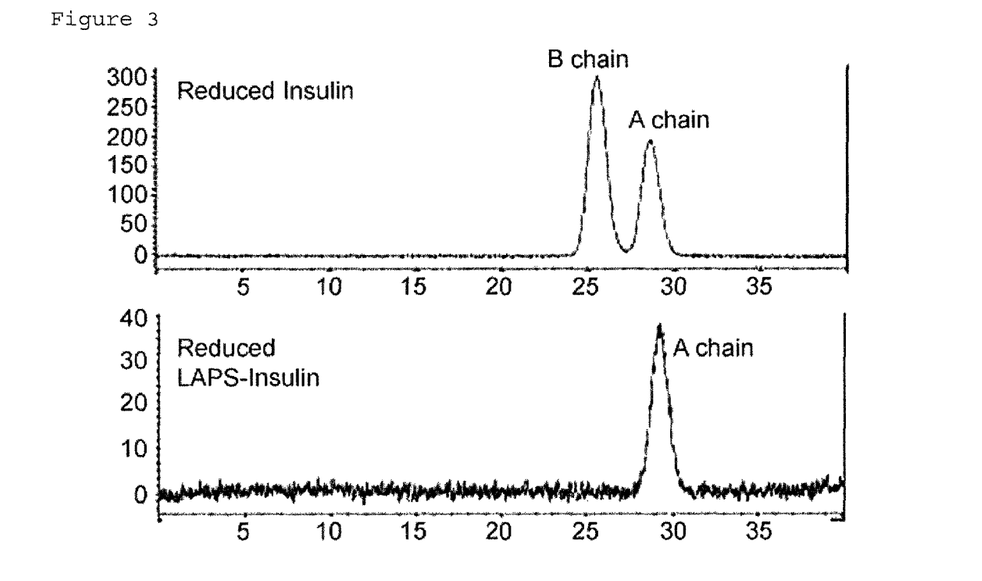
FIG. 3 is the result of analyzing 90% or more pegylation at phenylalanine (B1F) of the beta chain of insulin-PEG-immunoglobulin Fc conjugate using a size exclusion column.

To prepare an insulin-PEG-immunoglobulin Fc conjugate having 90% or more pegylation at phenylalanine (B1F) of the beta chain of insulin, the mono-PEGylated immunoglobulin Fc obtained in Example 1 and insulin were reacted at a molar ratio of 4:1 and at 4° C. for 20 hrs, with a total protein concentration of 20 mg/ml. At this time, the reaction was performed in a 100 mM potassium phosphate buffer solution at pH 6.0, and 20 mM SCB as a reducing agent was added thereto. After the reaction was terminated, the reaction solution was subjected to primary purification using a Source 15Q column. Thereafter, secondary purification was performed using a Source 15ISO column to obtain an insulin-PEG-immunoglobulin Fc conjugate. A size exclusion column was used to analyze 90% or more pegylation of B1F of the obtained insulin-PEG-immunoglobulin Fc conjugate, and the results are shown in FIG. 3.

Example 3

Preparation of Insulin Lispro (Humalog)-PEG-Immunoglobulin Fc Conjugate

The mono-PEGylated immunoglobulin Fc obtained in Example 1 and insulin lispro were reacted at a molar ratio of 4:1 and at 4° C. for 20 hrs, with a total protein concentration of 20 mg/ml. At this time, the reaction was performed in a 100 mM potassium phosphate buffer solution at pH 6.0, and 20 mM SCB as a reducing agent was added thereto. After the reaction was terminated, purification was performed in the same manner as in Example 2.

Example 4

Preparation of Insulin Glargine (Lantus)-PEG-Immunoglobulin Fc Conjugate

The mono-PEGylated immunoglobulin Fc obtained in Example 1 and insulin glargine were reacted at a molar ratio of 4:1 and at 4° C. for 20 hrs, with a total protein concentration of 20 mg/ml. At this time, the reaction was performed in a 100 mM potassium phosphate buffer solution at pH 6.0, and 20 mM SCB as a reducing agent was added thereto.

After the reaction was terminated, purification was performed in the same manner as in Example 2.

Example 5

Preparation of Insulin Detemir (Levemir)-PEG-Immunoglobulin Fc Conjugate

The mono-PEGylated immunoglobulin Fc obtained in Example 1 and insulin detemir were reacted at a molar ratio of 4:1 and at 4° C. for 20 hrs, with a total protein concentration of 20 mg/ml. At this time, the reaction was performed in a 100 mM potassium phosphate buffer solution at pH 6.0, and 20 mM SCB as a reducing agent was added thereto. After the reaction was terminated, purification was performed in the same manner as in Example 2.

Example 6

Measurement of In Vivo Elimination Half-Life of Long-Acting Insulin Conjugate

Figure 1:
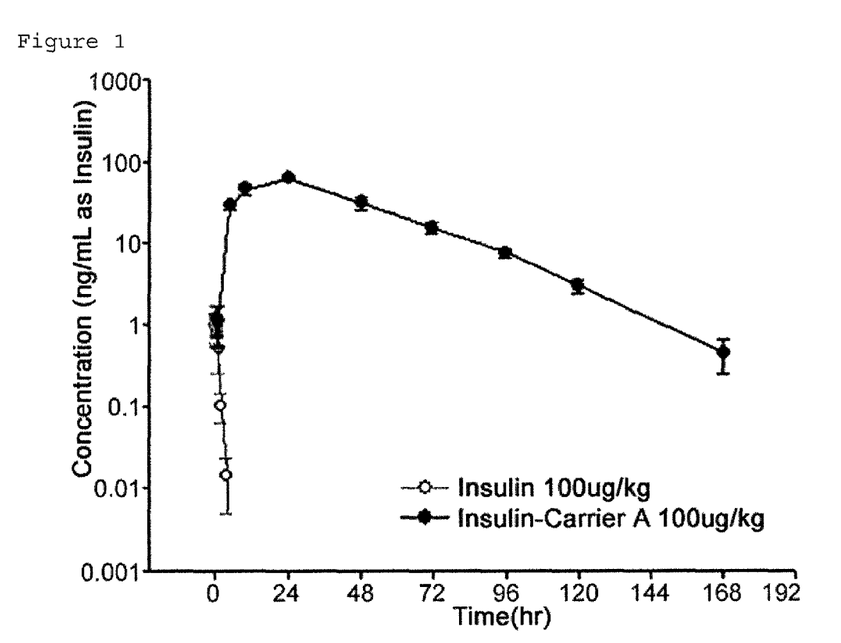
FIG. 1 is the result of pharmacokinetic analysis of insulin-PEG-immunoglobulin Fc conjugate.

To analyze in vivo duration of the long-acting insulin conjugate, normal male SD rats were used to perform pharmacokinetic analysis. Normal male SD rats were subcutaneously injected with native insulin and the long-acting insulin conjugate at a dose of 100 µg/kg (based on insulin) once, and then time-dependent changes in serum level were measured using an ELISA kit, and pharmacokinetic parameters were calculated from the measured values using Winnolin 5.2 software. The in vivo elimination half-life of the long-acting insulin conjugate was 17.67 hrs, which is about 30-fold longer than the native insulin of 0.58 hrs (FIG. 1).

Example 7

In Vivo Efficacy Test on Conjugate of Insulin Derivative

Figure 2:
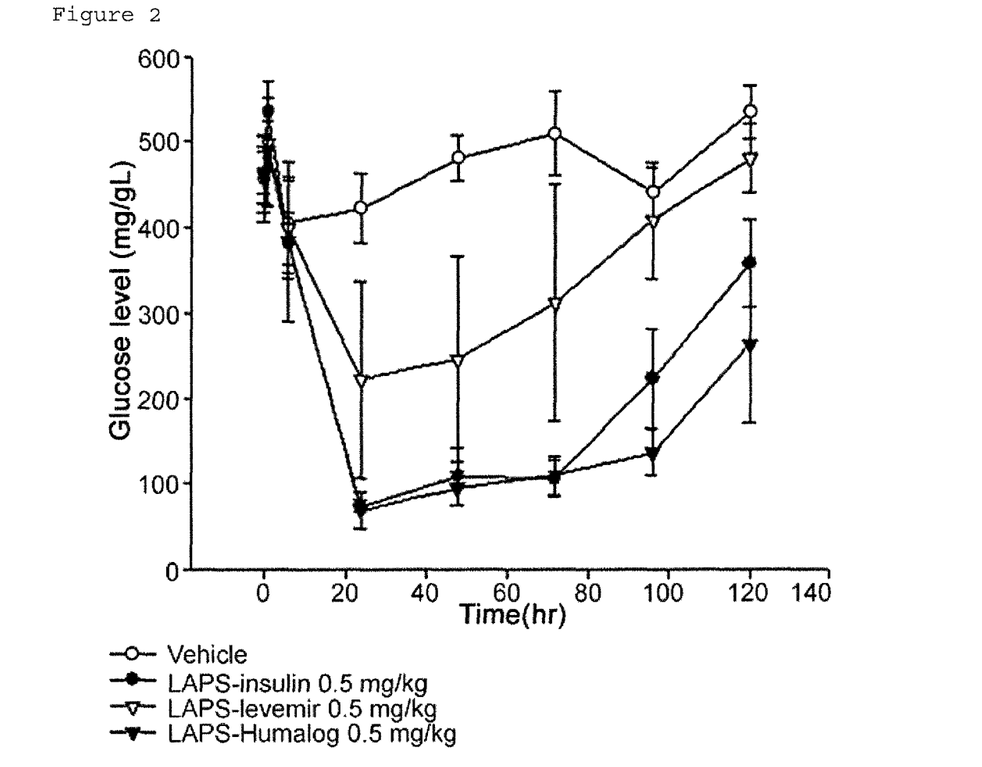
FIG. 2 is the result of comparing in vivo efficacies between insulin derivative-PEG-immunoglobulin Fc conjugates.

To compare in vivo efficacy between the conjugates of insulin derivatives, streptozotocin-induced diabetes rats were used to analyze their hypoglycemic effects. Normal rats were fasted for 16 hrs, and intraperitoneally injected with streptozotocin in 10 mM citric acid buffer solution (pH 4.5) at a dose of 60 mg/kg to induce diabetes. When the blood glucose level of the rats reached to 500 mg/dL or higher, the rats were subcutaneously injected with the insulin conjugate, the insulin detemir conjugate, or the insulin lispro conjugate at a dose of 0.5 mg/kg once, and then their hypoglycemic effects were compared. The hypoglycemic effects of the insulin conjugate and the insulin lispro conjugate maintained for about 4 days after injection, and 5 days after injection, the blood glucose level increased. The insulin detemir conjugate also showed the hypoglycemic effects, but the effects were lower than those of insulin conjugate or insulin lispro conjugate at an equal dose (FIG. 2).

Example 8

Identification of Binding Site of Insulin-5 K PEG-Immunoglobulin Fc Conjugate

Figure 4A:
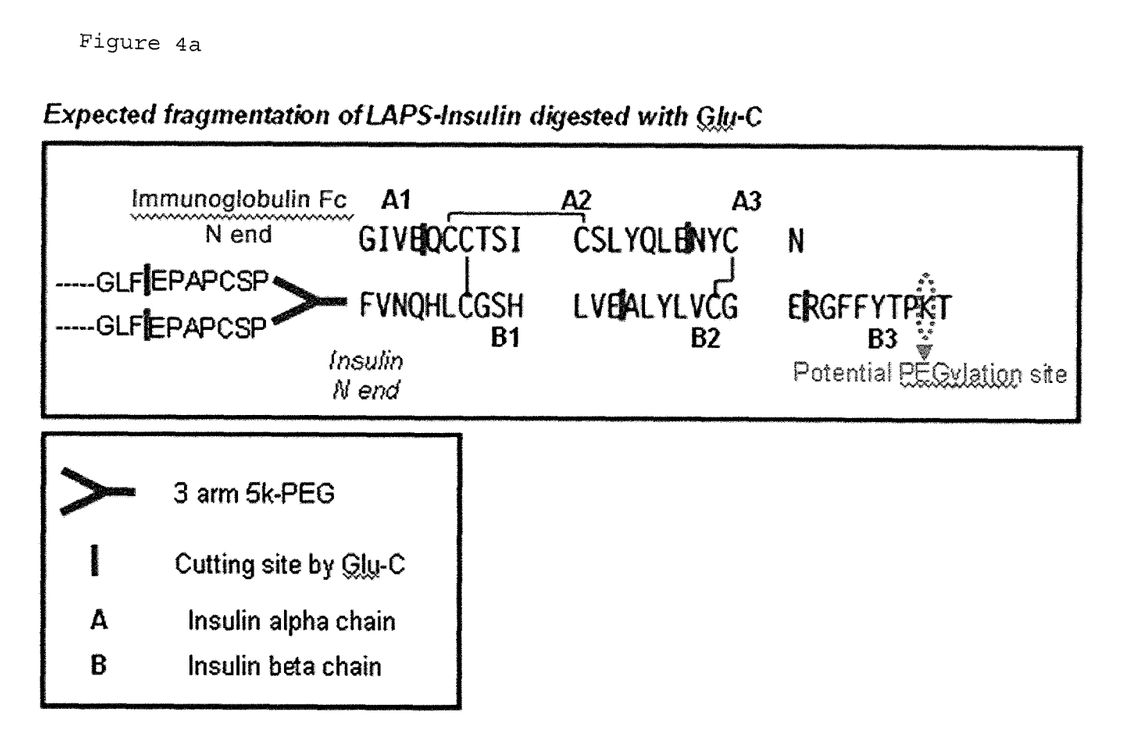
FIGS. 4a to 4c are the result of analyzing the beta chain-specific binding of insulin-PEG-immunoglobulin Fc conjugate.
Figure 4B:
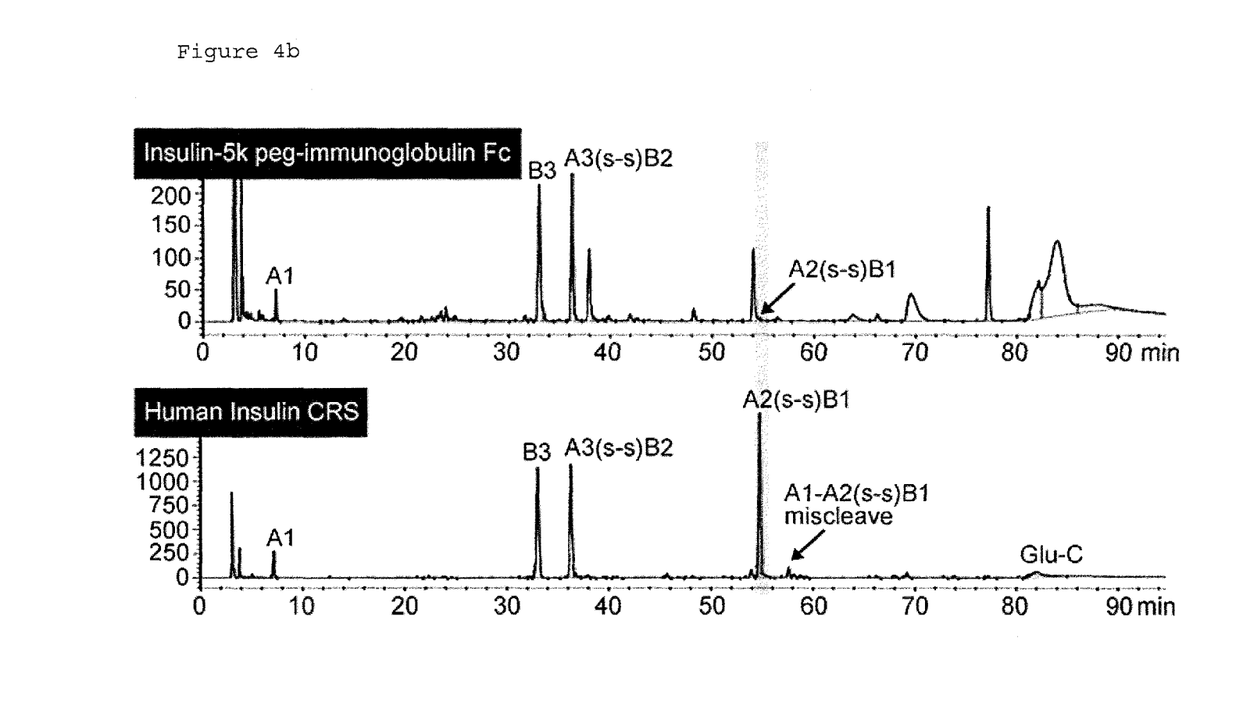
Figure 4C:
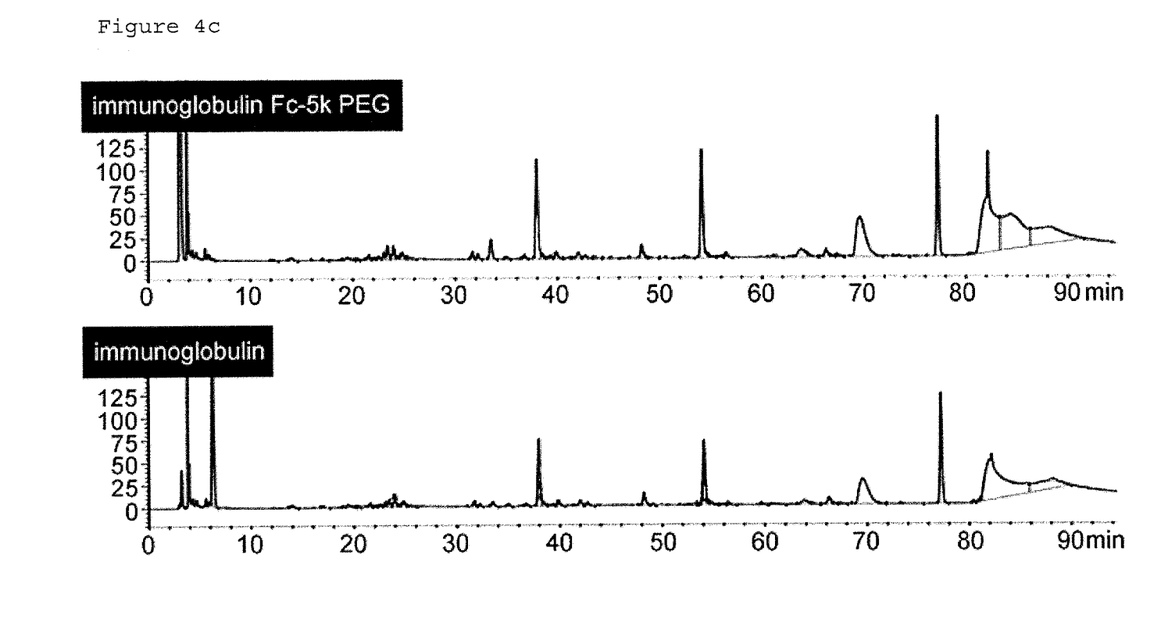

In order to identify the binding site of insulin to 5 K PEG-immunoglobulin Fc, Glu-C mapping was performed. 20 µg of endoproteinase Glu-C (1 mg/ml) was added to 100 µg of insulin-5 K PEG-immunoglobulin Fc (1 mg/ml). The reaction solution was 50 mM HEPES at pH 7.5, and the mixture was reacted at 25° C. for 8 hrs. Subsequently, 10 µl of 1 N HCL was added to terminate the reaction. Mapping was performed by reverse HPLC chromatography. The results showed the peak change in the N-terminus of beta chain of insulin, indicating that 5 K PEG-immunoglobulin Fc binds to the N-terminus of beta chain of insulin (FIGS. 4a-c).

Column: Jupiter C18 4.6×250 mm, 5 µm (Phenomenex)
Mobile phase A: 20% 0.1 M NaSO4 (pH 2.0), 10% CAN
Mobile phase B: 20% 0.1 M NaSO4 (pH 2.0), 40% CAN
Gradient 0% B in 10 min>0-10% B in 5 min>10-70% B in 60 min

---

The invention claimed is:

1. An insulin conjugate prepared by linking insulin with an immunoglobulin Fc region via a non-peptidyl polymer, in which the non-peptidyl polymer is linked to the phenylalanine at position 1 of amino terminal of beta chain of insulin, wherein the non-peptidyl polymer is polyethylene glycol and has a molecular weight in the range of 5 to 100 kDa,
   wherein the immunoglobulin Fc region consists of an immunoglobulin G4 Fc region,
   and wherein the insulin conjugate has an improved in vivo duration, stability and extended hypoglycemic effect compared to the insulin, and the insulin conjugate maintains in vivo activity of insulin.

2. The insulin conjugate according to claim 1, wherein the insulin is native insulin, or a variant, derivative, or fragment thereof that is prepared by any one method of substitution, addition, deletion, and modification or combinations thereof in amino acids of native insulin.

3. The insulin conjugate according to claim 1, wherein each end of the non-peptidyl polymer is linked to an amine group or thiol group of the immunoglobulin Fc region and insulin.

4. The insulin conjugate according to claim 1, wherein the immunoglobulin Fc region is aglycosylated.

5. The insulin conjugate according to claim 1, wherein the immunoglobulin G4 Fc region is composed of one to four domains selected from the group consisting of CH1, CH2, CH3 and CH4 domains of immunoglobulin G4.

6. The insulin conjugate according to claim 5, wherein the immunoglobulin Fc region further comprises a hinge region.

7. The insulin conjugate according to claim 1, wherein the immunoglobulin G4 Fc region is a human aglycosylated IgG4 Fc region.

8. The insulin conjugate according to claim 1, wherein the reactive group of the non-peptidyl polymer is selected from the group consisting of an aldehyde group, a propionaldehyde group, a butyraldehyde group, a maleimide group, and a succinimide derivative.

9. The insulin conjugate according to claim 8, wherein the succinimide derivative is succinimidyl propionate, succinimidyl carboxymethyl, hydroxy succinimidyl, or succinimidyl carbonate.

10. The insulin conjugate according to claim 8, wherein the non-peptidyl polymer has a reactive aldehyde group at both ends.

11. A long-acting insulin formulation having improved in vivo duration and stability, comprising the insulin conjugate of claim 1.

12. The long-acting insulin formulation according to claim 11, wherein the formulation is used for the treatment of diabetes.

13. A method for treating a subject having an insulin-deficiency disorder, the method comprising of administering to the subject an effective amount of the long-acting formulation of claim 11.

14. The method according to claim 13, wherein the insulin-deficiency disorder is diabetes.

15. A method for preparing the insulin conjugate of claim 1, comprising the steps of:
   (1) covalently linking a non-peptidyl polymer having a reactive group of aldehyde, maleimide, or succinimide derivatives at each end thereof, with an amine group or thiol group of an immunoglobulin Fc region;
   (2) isolating a conjugate from the reaction mixture of (1), wherein the conjugate comprises the immunoglobulin Fc region covalently linked with the non-peptidyl polymer; and
   (3) covalently linking insulin to the other end of the non-peptidyl polymer of the isolated conjugate to produce a peptide conjugate comprising the immunoglobulin Fc region and insulin that are linked to each end of the non-peptidyl polymer,
   wherein the non-peptidyl polymer is polyethylene glycol and has a molecular weight in the range of 5 to 100 kDa,
   wherein the immunoglobulin Fc region consists of an immunoglobulin G4 Fc region.

16. A method for preparing the insulin conjugate of claim 1, comprising the steps of:
   (1) covalently linking a non-peptidyl polymer having an aldehyde reactive group at each end thereof to the N-terminus of an immunoglobulin Fc at pH 6.0;
   (2) isolating a conjugate from the reaction mixture of (1), wherein the conjugate comprises the immunoglobulin Fc region covalently linked with the non-peptidyl polymer at its N-terminus; and
   (3) covalently linking insulin to the other end of the non-peptidyl polymer of the isolated conjugate to produce a peptide conjugate comprising the immunoglobulin Fc region and insulin that are linked to each end of the non-peptidyl polymer,
   wherein the non-peptidyl polymer is polyethylene glycol and has a molecular weight in the range of 5 to 100 kDa,
   wherein the immunoglobulin Fc region consists of an immunoglobulin G4 Fc region.

17. A method for preparing the insulin conjugate of claim 1, comprising the steps of:
   (1) covalently linking a non-peptidyl polymer having a reactive group of aldehyde, maleimide, or succinimide derivatives at each end thereof, with an amine group or thiol group of insulin;
   (2) isolating a conjugate from the reaction mixture of (1), wherein the conjugate comprises insulin covalently linked with the non-peptidyl polymer; and
   (3) covalently linking an immunoglobulin Fc region to the other end of the non-peptidyl polymer of the isolated conjugate to produce a peptide conjugate comprising the immunoglobulin Fc region and insulin that are linked to each end of the non-peptidyl polymer,
   wherein the non-peptidyl polymer is polyethylene glycol and has a molecular weight in the range of 5 to 100 kDa,
   wherein the immunoglobulin Fc region consists of an immunoglobulin G4 Fc region.

* * * * *

SEQUENCE LISTING

```
<160> NUMBER OF SEQ ID NOS: 2

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
 1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
 1               5                   10                  15

Leu Val Cys Gly Glu Arg Gly Phe Phe Tyr Thr Pro Lys Thr
            20                  25                  30
```